United States Patent [19]

Brown

[11] Patent Number: 5,445,622

[45] Date of Patent: Aug. 29, 1995

[54] FLOW SWITCH DEVICE FOR MEDICAL APPLICATIONS

[76] Inventor: Eric W. Brown, 98 Baycrest Ct., Newport Beach, Calif. 92660

[21] Appl. No.: 360,994

[22] Filed: Dec. 20, 1994

[51] Int. Cl.6 .............................................. A61M 5/00
[52] U.S. Cl. ..................................... 604/246; 604/65; 128/DIG. 13
[58] Field of Search ................... 604/246, 247, 65–67, 604/207, 118, 131; 128/DIG. 12, DIG. 13

[56] References Cited

U.S. PATENT DOCUMENTS

| | | | |
|---|---|---|---|
| 4,976,687 | 12/1990 | Martin | 604/246 X |
| 5,356,378 | 10/1994 | Doan | 604/65 |
| 5,376,070 | 12/1994 | Purvis et al. | 604/65 X |
| 5,395,320 | 3/1995 | Padda et al. | 604/65 |

*Primary Examiner*—John D. Yasko
*Attorney, Agent, or Firm*—Macro-Search Corp.; Gene Scott

[57] ABSTRACT

An intravenous system for monitoring the flow of IV fluids to a patient is embodied in a wristwatch sized unit for placement on the patient. The device includes a flow indicator switch capable of detecting when flow starts or stops. In one embodiment, the range of flow rates which may trigger a signal is increased using a plurality of sensor elements. The flow indicator switch uses a conical chamber with a movable flow element which reacts to the motion of the IV fluid. A light emitter-sensor arrangement provides a means for converting physical displacement into an electrical signal indicating displacement of the movable member.

10 Claims, 7 Drawing Sheets

FLOW SWITCH DEVICE FOR MEDICAL APPLICATIONS

FIELD OF THE INVENTION

This invention relates to intravenous (IV) fluid delivery systems and in particular to a monitoring device for providing information on when and if the delivery of an IV fluid to a patient actually occurred.

BACKGROUND OF THE INVENTION

The rapid rise of health care costs has become an important issue in modern society. To help reduce the costs, professional care givers have begun to seek alternatives, one of which is home health care services. These services not only tend to reduce costs, but are also preferred by the patient wishing to remain in his familiar environment. Among the many types of services provided are: respiratory care, rehabilitation therapy, cardiac monitoring procedures, and infusion therapy.

Infusion therapy involves IV administration of drugs. Making this therapy safe and convenient for a home situation allows a great number of patients who would otherwise be hospitalized to remain at home and still receive medication. Currently, over 300,000 patients annually use a home infusion therapy delivery system. Typically, patients include the elderly with chronic diseases like cancer, patients with either Crohns disease, HIV or other immune system disorders, and patients suffering from chronic pain. Many of these patients require infusion treatment over a long duration such as months or even years.

One characteristic of home IV drug therapy, in contrast to hospital administered therapy, is that a nurse is not always present or readily available. To provide safe and effective treatment, home infusion therapy usually requires that the patient himself, or other non-professional caregiver, such as a relative, administer IV fluids. Special training is required because many home care patients on IV therapy require multiple drugs or multiple doses of the same drug each day. The average nursing visit to a home infusion therapy patient is typically about 90 minutes including commuting time. The typical patient gets between 1 and 4 nursing visits per week, but has to take IV medications daily. Since the cost of daily care by a nurse is not usually covered by most insurers, the cost of attention by a nurse is most economically applied in training the patent or other amateur caregiver and in monitoring the therapy program.

In the home care situation non-compliance, over-medication or under-compliance with the IV therapy protocol is a serious issue and quite prevalent. For instance, non-compliance (not taking a medication) or under compliance (taking fewer or smaller dosages than prescribed) occurs in up to approximately one-third to one-half of elderly home therapy patients. Typical compliance related problems include forgetting to follow the specified procedure for administration of the IV medication, forgetting to turn on the various devices used to administer the IV medication and forgetting to turn off a medical device which then delivers too much medication (over-medication). Reasons for compliance related problems are varied and include poor communication, confusion or forgetfulness regarding the procedures and/or equipment, or even attempts to avoid the adverse side effects of IV medications and fluids. Misapplication of the home IV therapy protocol can have serious ramifications resulting in greatly increased home health care nursing expenses, re-hospitalization, and reduction in health status of the patient. Thus, there is a strong need for improved monitoring of patient compliance with the health care program. Benefits of such improved monitoring and compliance include, but are not limited to, improved health at a lower cost, while still remaining in the preferred home environment.

To properly monitor compliance with an IV therapy protocol, a device may be provided for monitoring the flow of IV medications and fluids. The IV fluids for a single patient are likely to come from several different sources or systems including IV pumps, IV fluid controllers, gravity drips, syringes, and other devices.

A typical gravity powered IV may be as simple as an IV bag hanging on a pole in which a nurse or care giver manually adjusts a valve to limit the flow rate, but not control it accurately, or it may use an electronic controller which optically counts the drops of fluid as they pass an optical sensor and then adjusts the flow rate accordingly. However, optical drop counting sensors only provides an indication that the fluid is flowing past the sensor when in a vertical orientation such as hanging from an IV pole. Thus the patient and IV delivery equipment must remain relatively stationary during the administration of the medication or fluid. Optical drop counters also function poorly at higher flow rates and higher line pressures, such as when a syringe is used, because the fluid moving past the drop counter tends to become a continuous stream rather than remaining discrete drops. Therefore, the optical drop counter technique cannot be adapted for use with all fluid sources.

An alternative to an optical drop counting sensor, or as a stand-alone measuring device, is a single point pressure transducer to measure the fluid pressure in the IV tubing at a selected point of measurement. This type of sensor is common in IV pumps and is used to indicate that the pump is generating a static pressure head and, correspondingly, causing fluid flow or backpressure in the event of an occlusion in the IV line. This type of sensor only determines line pressure at the selected point, and is only useful in monitoring the pressure caused by the IV pumping device and the related backpressure caused by moving fluids into the patient's body. However, this type of single-point pressure sensor is useful in many IV delivery systems to determine if fluid pressures are at correct levels, and to detect changes in fluid pressure which are indicative of an occluded or collapsed vein. Often, when a certain threshold pressure is detected in a device using this type of sensor, an alarm is sounded to warn of a flow problem. This type of device measures changes in the static line pressure of a fluid line, but is unable to determine if a patient is following proper IV drug administration procedures and cannot differentiate between changes in pressure due to fluid flow versus some other cause, such as an occlusion in which there is actually no fluid flow.

Increased backpressure in an IV fluid line causes problems, and, as described above, many IV fluid delivery systems use a sensor to determine when high backpressure develops, i.e., greater than a few inches of water, for instance when an infiltration of tissue occurs or the tubing becomes occluded. Upon the detection of a significant backpressure, the device sounds an alarm and may function to automatically discontinue the delivery of the IV medication and fluids. Therefore, it is important that any device used to monitor whether or not fluid is flowing does not cause a substantial increase in backpressure or a false occlusion alarm might be triggered.

Other alternatives use indirect methods to monitor the flow of IV fluids. For instance, the speed and number of rotations in a pump mechanism may be monitored to indirectly determine when fluid flow is occuring. This is useful for flows caused by an IV pump, but is of no value to patients who also receive gravity drips or fluids via syringe. Since nearly all infusion therapy patients must perform venous access device maintenance procedures, such as a heparin flush via syringe to maintain the patency of their IV lines, this pump rotation technique is not of value for monitoring all infusions.

The time usage for an IV delivery system may be recorded to prepare bills to patients. Typically, the information is printed or stored in an electronic memory device such as the electronic controls for the drop counter or IV pump. The information may be used to determine which of several patients are using the IV system being monitored, it may be used to coordinate several IV delivery systems with a centrally managed pump, or it may be used to facilitate billing and reimbursement. Unfortunately, none of these systems accommodate tracking of fluid delivered from a variety of sources such as to a patient who receives syringes, gravity drips, and IV pump infusions. The present invention provides an improved flow indicator switch, which overcomes the above-mentioned limitations of the prior art.

SUMMARY OF THE DISCLOSURE

The present invention is an IV system which provides certain monitoring advantages. An electronic data processing and storage device is used in conjunction with a unique flow indicator switch to record events in the IV infusion process. The processor may be connected in real time or may be used simply as a data recorder for later analysis. If used in real time the processing device is used to interpret signals related to IV flow, to provide instructions on how to properly sense whether fluid flow is occurring, and on when to inform the user to use the IV system or even to take other medications, vis-a-vis, oral or injection therapy, etc.

In the preferred embodiment of the present invention, an IV infusion system provides a flow indicator to monitor a flow of fluid through a fluid flow path. The flow indicator includes a switch having a movable switch member that is forced to move by direct viscous forces against it within the flow path, so that it moves in the direction of fluid flow. The movable switch member can sense a change in system flow including positive flow startup from stagnation in order to indicate that fluid flow has stopped or started. Optical elements including an infrared emitter and detector sense the change of position of the movable switch member. A spring element provides a restoring force to return the movable switch member to a null position indicating "no flow" when fluid flow has ceased. The force exerted by the spring element is adjusted to sense flow rates as low as 3.0 milliliters per hour.

Further, the flow indicator switch has a variable orifice positioned in a shaped fluid passageway in the form of an annulus. The orifice changes in cross-sectional size depending upon the position of the movable switch member. The cross-sectional area of the orifice is designed to enhance sensitivity to low fluid flows when the orifice has a smaller cross-sectional area, as well as to limit backpressure generated by higher fluid flow when the orifice has a larger cross-sectional area. In the preferred embodiment, the increase in backpressure is limited to about 4 inches of water with flow rates as high as 3600 milliliters per hour. In the preferred embodiment, the flow indicator switch functions equally well at line pressures from a fraction of an inch of water to over 60 pounds per square inch pressure because no occlusion of the flowpath occurs. Therefore, the flow indicator switch is not an occlusive device and does not react to changes in static pressure.

The processor is preferably operationally coupled to the flow indicator switch, to monitor the time and date of starts and stops of IV fluid flow in the system. One preferred embodiment of the present invention provides for the processor to be housed in a case about the size of a wrist watch so that it is highly portable for wearing on the person. This provides several key advantages and benefits to the infusion patient which would not otherwise become possible.

The processor and the flow indicator may be operationally coupled by fluid conduits, electrical conductors, wireless transmitters and receivers, or the like. The processor includes a memory storage device which retains information related to the programmed IV protocol and the actual time of start and stop events. The processor may of course be interconnected with a computer or other high speed data device for data archiving purposes and for further data analysis. In the preferred embodiment, the processor is serially coupled with a notebook PC that downloads prescribed IV protocols and uploads actual fluid flow start/stop events for comparison. The downloaded and uploaded data may include fluid flow events from any or all sources of fluid including, but not limited to, IV pumps, gravity drips, and syringes.

The flow indicator switch may operate in any attitude providing an advantage over prior apparatus. Moreover, the flow indicator switch housing is formed with a fluid flow path that is easily de-aired by a flow of fluid through the flow indicator switch housing. The flow indicator switch is a passive device, in which the movable switch member is actuated by the fluid flow through the tube. It can have a sensitivity to low fluid flows of less than or equal to 3.0 milliliters per hour and a backpressure limited to less than or equal to 4.0 inch of water line pressure at higher flow rates common to intravenous drug therapy, such as 3600 milliliters per hour. The flow indicator switch can work well with pulsed fluid flows without triggering a false alarm in the fluid delivery equipment.

Another advantage is that the small size and portability of the flow indicator switch precludes the necessity of having the patient attach and detach the device each time it is used. It may be attached to the patient's IV catheter for long periods of time. Also, since it is a passive device, it requires less electrical power and maintenance, thereby reducing health care costs. It may be connected to a catheter or IV tubes by standard connectors typically used on common IV equipment, or it may be an integral part of the IV catheter tube assembly.

Other features and advantages of the invention will become apparent from the following detailed description, taken in conjunction with the accompanying drawings which illustrate, by way of example, various features of the several embodiments of the invention.

BRIEF DESCRIPTION OF THE DRAWINGS

A detailed description of embodiments of the invention will be made with reference to the accompanying drawings, wherein like numerals designate corresponding parts in the several figures, in such drawings.

DETAILED DESCRIPTION OF THE PREFERRED EMBODIMENTS

Figure 1:
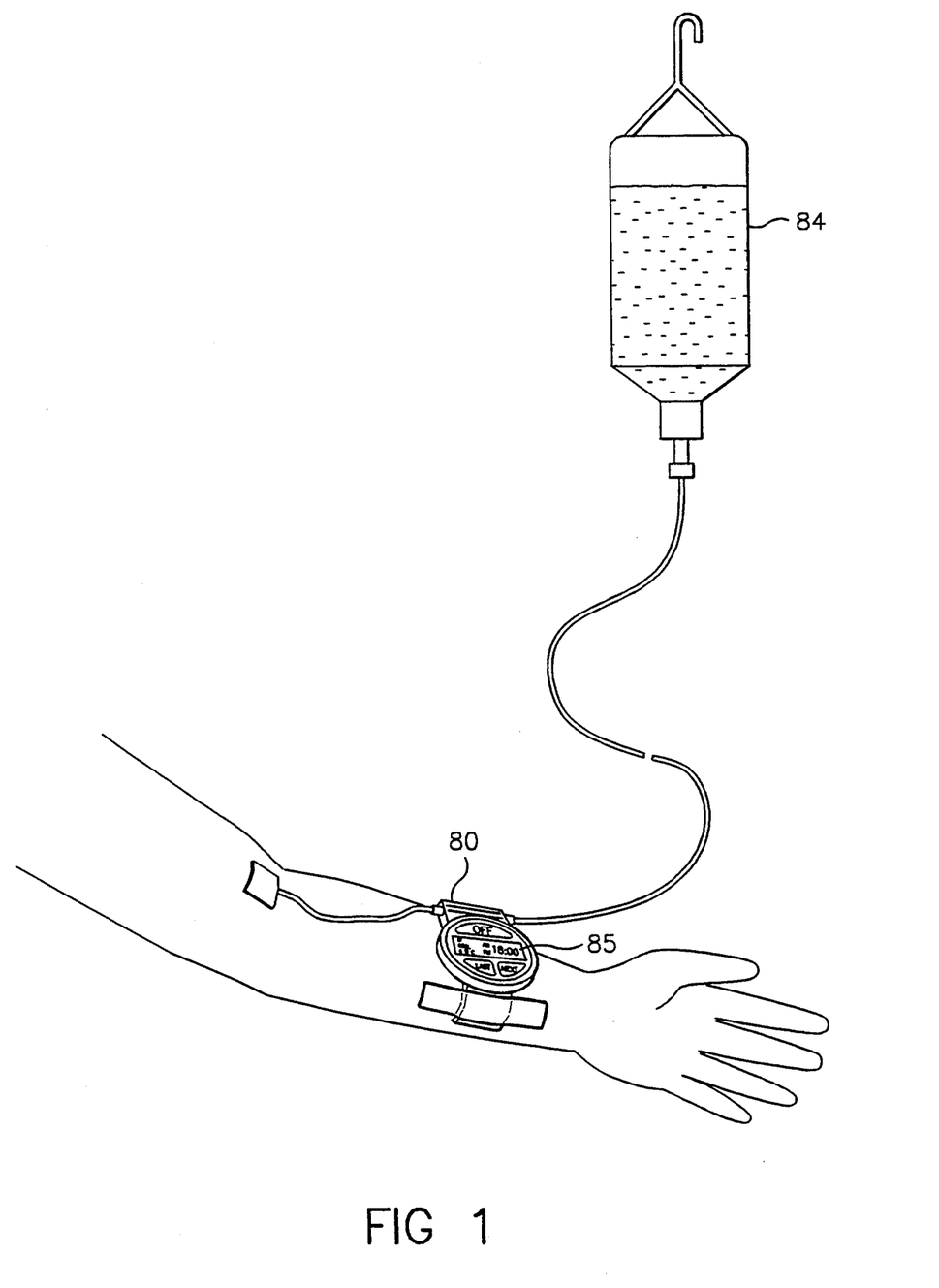
FIG. 1 is a perspective view showing on overview of the present invention in a general orientation as applied to a patient in a wrist or arm mounted embodiment.

FIG. 1 shows an intravenous system for conducting an IV fluid and for monitoring its flow, thus providing information on the delivery of,an IV fluid to a patient. Preferably, the device has a wristwatch sized event monitor 80 that attaches to a patient's arm or that may be taped to the patient's chest depending upon the site of the IV catheter. Event monitor 80 provides a display 85 that is easily viewed by the patient. As shown more clearly in FIG. 5, the display 85 can indicate the current time and date; the time and date of the next IV infusion process including which of 3 drugs to use; and the time and date of the last IV infusion process performed. The display 85 also may show similar information about oral medications, and the event monitor may also remind the patient to take oral medications similar to the way an electronic pill bottle reminds patients when to take a pill.

The monitoring apparatus for the intravenous fluid delivery is a system comprised of two primary components. The first being the event monitor 80, used to store and record electronic data pertaining to fluid flow. The second component is a flow indicator switch 10, through which the monitored fluid passes and within which fluid stop and start events are detected by optical means. Alternately, another embodiment permits the monitoring of fluid flow rate.

Figure 2:
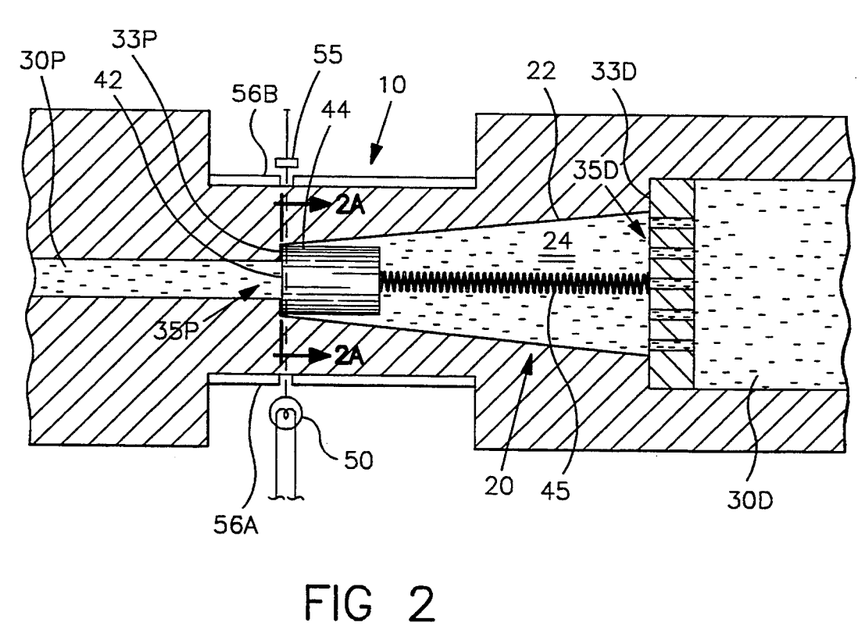
FIG. 2 is a schematic representation of a first prefered embodiment of the present invention of FIG. 1 shown as a simple flow indicator switch held within the case shown in FIG. 1, wherein some dimensions are shown exaggerated for better understanding of the principles involved, and particularly showing a flow conduit, inlet and outlet orifices, stem body, and light emitter and detector of the preferred embodiment.
Figure 2A:
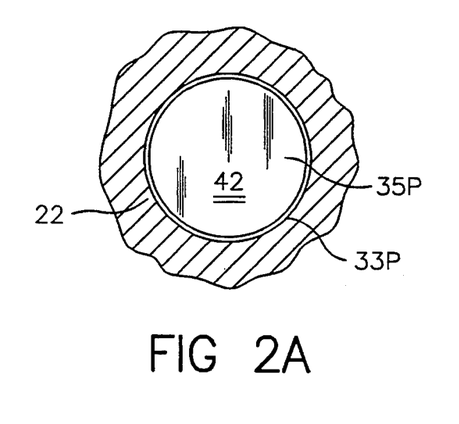
FIG. 2A is a cross-sectional view of the flow indicator switch taken along lines 2A—2A of FIG. 2 and particularly showing the preferred relationship between a proximal shoulder, the fluid conductor and an end of the stem body, wherein some dimensions are shown exaggerated for better understanding of the principles.
Figure 2B:
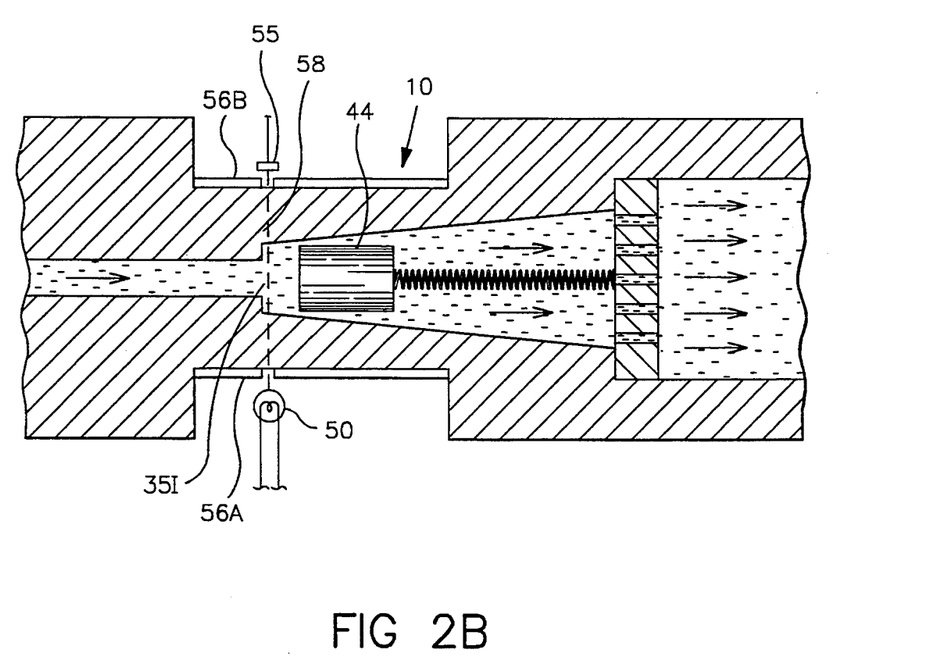
FIG. 2B is a schematic representation similar to that of FIG. 2 showing an alternate position of the stem body of the invention.

Referring now to FIGS. 2, 2A and 2B, an important component of the flow indicator switch 10 is shown as fluid conductor 20. The conductor 20 has a clear wall 22 that encloses a fluid space 24. The clear wall is advantageous for visually ensuring that air is removed from the IV fluid path. The fluid conductor 20 extends between proximal and distal fluid conduits 30P and 30D. An inlet interconnection means 87P connects the proximal conduit 30P to a source of intravenous fluid, preferably an IV bag 84, or a syringe (not shown) or an IV pumping device (not shown) well known to the field. An outlet interconnection means 87D connects the distal conduit 30D to an intravenous discharge device 88 that discharges the IV fluid to the patient's vein.

The conductor 20 has a conical shape having a slight wall divergence of approximately 0.3 to 2 degrees, so that it is larger at its distal end. A proximal and distal circular shoulders 33P and 33D are provided at the ends respectively of the conductor 20, the proximal shoulder 33P defining an inlet fluid orifice 35P, and the distal shoulder 33D defining an outlet orifice 3 5D.

In the preferred embodiment, an opaque stem body 40 for use with optically clear fluids, is a movable piston or plug element, and is provided within the fluid space 24 of the conductor 20. An alternate embodiment, to be discussed later, uses an optically clear stem body 40 for use with opaque fluids.

Figure 3:
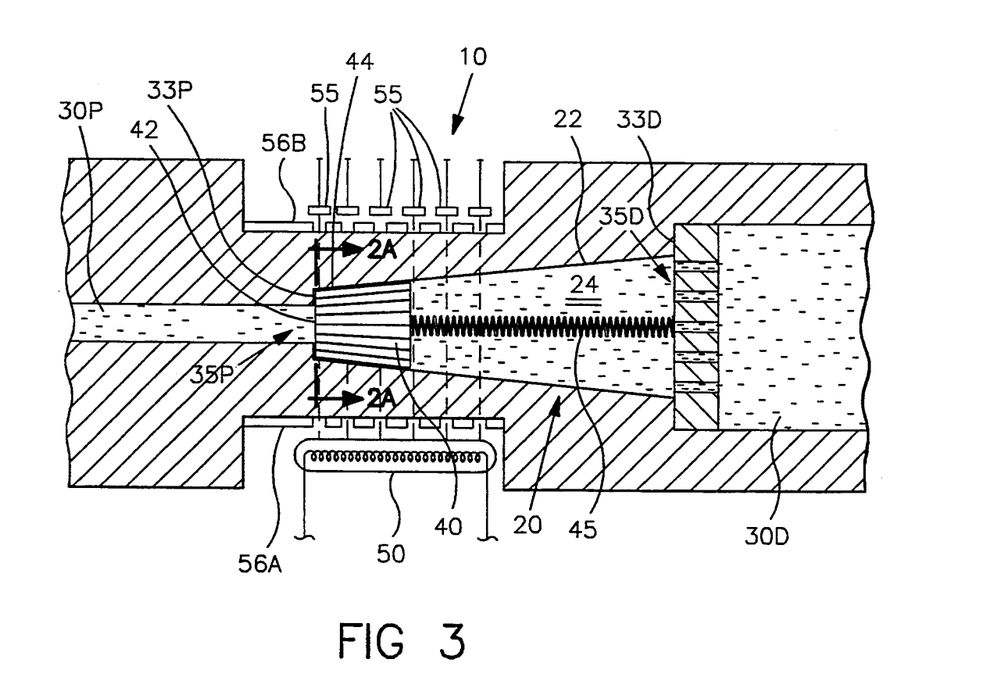
FIG. 3 is a schematic representation of a second prefered embodiment of the present invention of FIG. 1 shown as a flow rate indicator held within the case shown in FIG. 1, wherein some dimensions are Shown exaggerated for better understanding of the principles involved, and particularly showing a flow conduit, inlet and outlet orifices, stem body, and light emitter and detectors of the preferred embodiment.
Figure 3A:
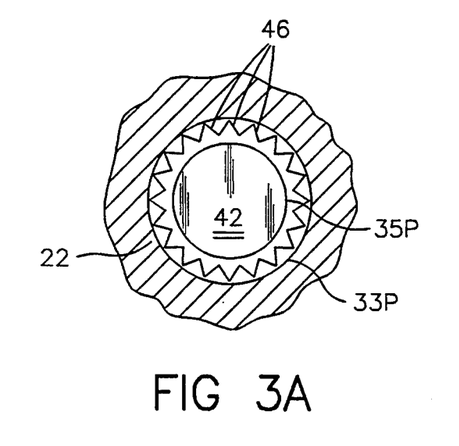
FIG. 3A is a cross-sectional view of the flow indicator switch taken along lines 3A—3A of FIG. 3 and particularly showing the preferred relationship between a proximal shoulder, the fluid conductor and an end of the stem body, wherein some dimensions are shown exaggerated for better understanding of the principles.
Figure 3B:
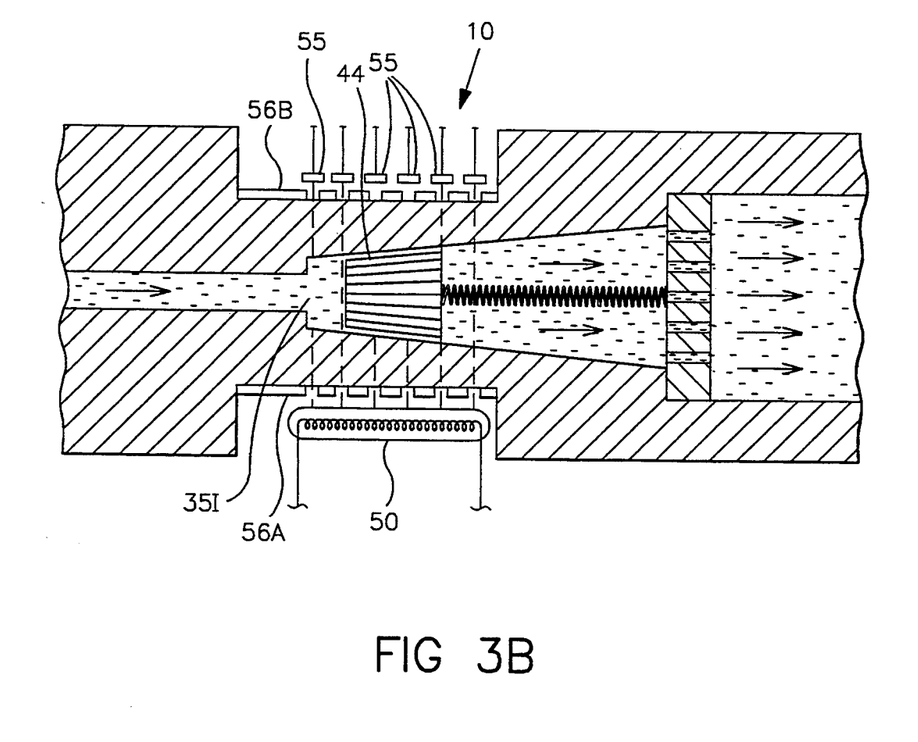
FIG. 3B is a schematic representation similar to that of FIG. 2 showing an alternate position of the stem body of the invention.
Figure 4:
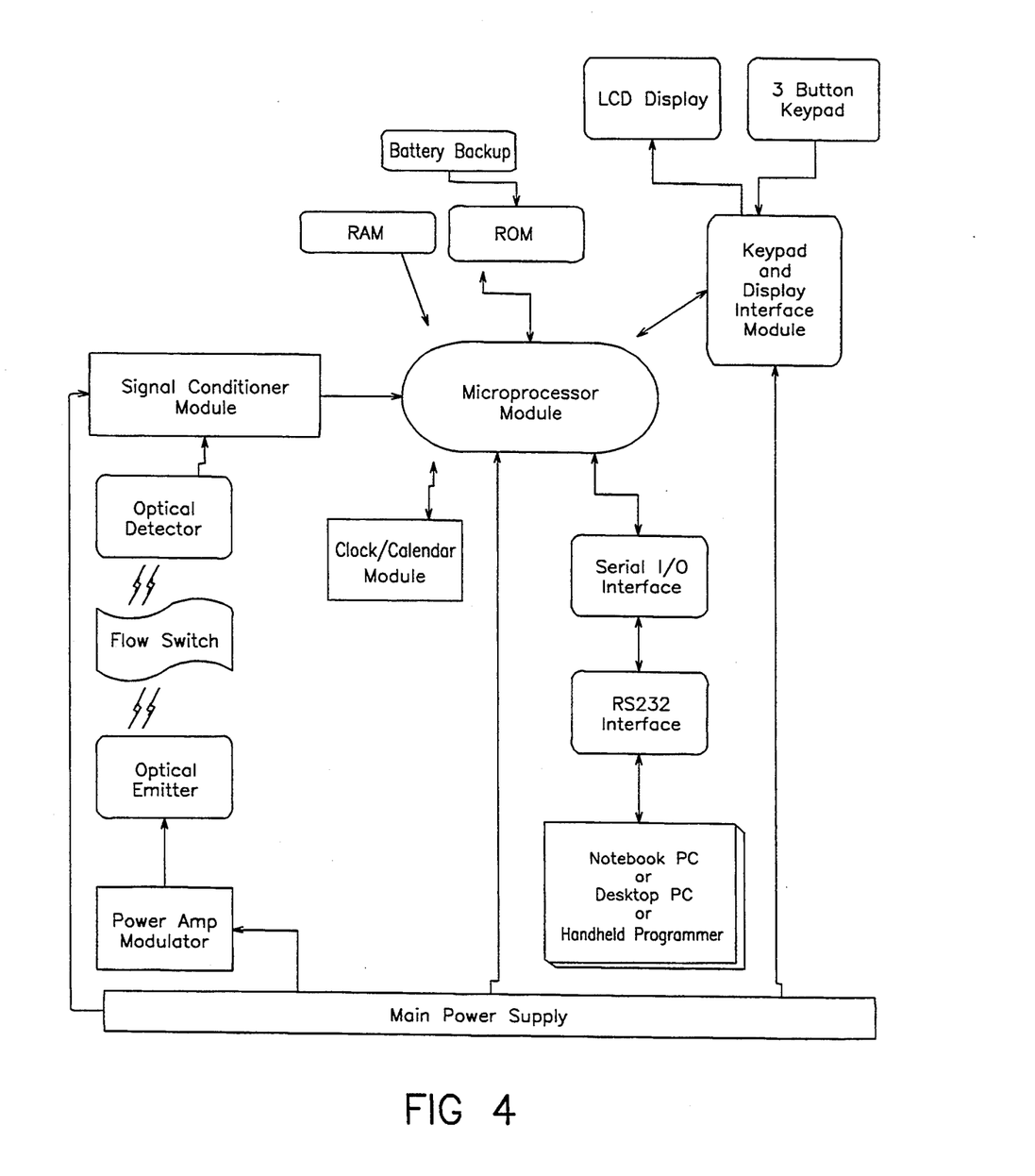
FIG. 4 is a general block diagram of an electronic circuit of the invention showing the preferred interconnections of various electrical elements of the invention.

In the preferred embodiment the body 40 has a volume of $6.8586 \times 10^{-3}$ cubic centimeters and a density of approximately 1.25 grams per cubic centimeter. As shown in FIG. 2, the stem body 40 preferably has a cylindrical shape which is slightly smaller in diameter than the conductor 20. When the stem body 40 is positioned at the proximal end of the conductor 20 abutting the proximal shoulder 33P, the stem body 40 does not engage any portion of the conical wall 22. The stem body 40 has a generally flat surface 42 at the end that contacts the proximal annular shoulder 33P, and may have a relatively smooth (FIG. 2A) or a ridged (FIG. 3 A) outer surface 44 that provides a series of fluid pathways 46. The surface 44 and fluid pathways 46 are shown in FIGS. 3 and 3A in an exaggerated manner. The preferred dimensional clearance between stem body 40 and the proximal shoulder 33P is about 0.0015 inches and this effective gap may often be accomplished by virtue of the natural texture or roughness of the surface of the materials without having to especially provide for grooved fluid pathways as shown in the aforementioned figures. A stem body biasing means 45, preferably a spring, urges the surface 42 of the stem body 40 in position against the proximal shoulder 33P, thus partially, but not fully, closing the fluid conductor 20 under static conditions. This partial closure allows at least some of the fluid to pass out of the indicator switch 10 in the direction away from the patient in the event that blood must be drawn from the patient or fluid must be removed from the line. It also allows for instantaneous equilibrium between pressure changes upstream or downstream of the stem body 40 in that upstream and downstream fluids are not mutually isolated. Occlusion of the flow path does not occur.

The spring constant of the biasing means 45 is preferably approximately 0.06 pounds per inch of deflection which means that the stem body 40 is displaced by a very slight flow of fluid into inlet 35P and out of outlet orifice 35D. It should be noted, however, that other spring constants and stem body masses may be selected for similar performance.

In the preferred embodiment shown in FIG. 2, a light emitter 50 is positioned outside of the conductor 20, lateral to the stem body 40, and a single light detector 55 is positioned directly across from the light emitter 50, on the opposite side of the conductor 20. As shown in FIG. 2, the left-hand side edge of the detector 55 is aligned with the proximal shoulder 33P and the base of the stem body 40. An opaque mask 56A is positioned between the light emitter 50 and the stem body 40, and another mask 56B is placed between the light detector 55 and the opposing side of the stem body 40. In another embodiment both masks 56A and 56B have tiny openings that are aligned in corresponding pairs in opposition across the fluid conductor. In the preferred embodiment, these openings are between 0.003 to 0.030 inches in diameter depending upon the power of the emitter 50 and the sensitivity of the detector 55 These openings in the masks 56A and 56B restrict light travel from the emitter 50, to a narrow light path 58 across the fluid conductor 20. As seen in FIG. 2, when the stem body 40 is in position against the proximal shoulder 33P, the light path 58 between the emitter 50 and the detector 55 is fully blocked by the opaque stem body 40, light is prevented from reaching the first light detector 55. However, as seen in FIG. 3, when the stem body 40 moves away from the proximal shoulder 33P, the light path 58 is provided. Thus, any change in position of the stem body 40 within fluid conductor 20 is easily determined by whether the light path 58 is blocked or not.

Although FIGS. 2 and 3 show an embodiment with a single light detector 55, any number of light detectors may be used as shown in FIGS. 6 and 7. In this alternative manner, an IV line with a constant flow, such as those used for KVO or "Keep Vein Open" applications, may be monitored for a meaningful change in flow rate. In the preferred embodiment, the emitter 50 and detectors 55 operate in infrared wavelengths.

As mentioned previously, in the preferred embodiment the stem body 40 is opaque in order to block the passage of light from the emitter 50 to the detector 55 when used with optically clear fluids. In certain instances however, a patient may receive IV fluids such as blood products or feeding solutions, that are not optically clear. The optical properties of these opaque solutions naturally attenuate light passing through them. This attenuation is proportional to the length of distance that the light must pass through the fluid. Therefore, an alternative embodiment of the stem body 40 uses a clear plastic which then limits the attenuation to that which occurs over a few thousandths of an inch. In this manner, the electronics may be modified to receive an optical signal for "no-flow" conditions and an opaque or blocked signal for "flow" conditions.

The intravenous system also includes a processor circuit 60 which may use a digital microprocessor chip to provide a logic program for interfacing the flow indicator switch into a therapeutic program of IV infusion and other medications. The circuit 60 preferably provides a means for using electrical signals from the light detector 55 to store IV fluid flow event information. Intermittently, it is possible that non-fluidic events, such as the motion of a patient, may cause spurious signals due to minor displacements of the stem body 40. Testing has shown that these spurious signals are of short duration, such as a fraction of a second. The Event Monitor 80 houses the processor circuit 60 which also includes logic for determining minimum "Flow On" time periods and intervals to remove most spurious signals from the log of flow events stored in memory.

Thus, in use, the proximal conduit 30P is connected to an IV bag or other fluid source, and the distal conduit 30D connects to an intravenous discharge device interconnected with a vein. Both conduits 30P and 30D and the conductor 20 are filled with IV fluid and desired prior to attaching to the patient, and the stem body 40 is nominally positioned against the proximal shoulder 33P indicating a no flow condition. The system remains static until flow from the IV bag or other fluid source is activated and the stagnation pressure due to fluid motion against the stem body 40 increases. The force on stem body 40 overcomes the restoring force of the biasing means 45, causing stem body 40 to move away from the proximal shoulder 33 P. This allows fluid which flows from the conduit 30P and through the inlet orifice 35P to be immediately sensed. The force of the fluid flow moves stem body 40 to a position within the fluid conductor 20 where a state of dynamic equilibrium is achieved between the force of fluid against stem body 40 and the restoring force. As stem body 40 moves further toward the distal end of the fluid conductor 20, as is typical at higher flow rates, the annular flow path area between the stem body 40 and the conical conductor wall 22 becomes larger, thereby increasing flow conductance in the conductor 20. Therefore a nonlinear relationship is developed between stem body displacement and conductance such that backpressure is minimized very quickly.

In particular, when the stem body 40 is positioned against the shoulder 33P, as shown in FIG. 2, it blocks light from arriving at the leftmost edge of light sensor 55. This leftmost edge of light sensor 55 is particularly of interest in establishing if fluid in the system is static, or is flowing. Further, the amount of light reaching the leftmost edge of light sensor 55 does not have to saturate the photodector means in light sensor 55. In the preferred embodiment, a signal of about 300 millivolts is generated when the light sensor 55 is fully saturated with light when both tiny openings 56A and 56B are fully exposed. However, an almost minuscule change in position of stem body 40 will cause a smaller change in voltage from 0.0 millivolts (totally opaque) to 0.5 millivolts because the leftmost edge of light sensor 55 is partially illuminated. This smaller change is voltage is used to determine that fluid motion has commenced or ceased. Thus the signal induced by the leftmost edge of light sensor 55 is used in the preferred embodiment to determine the "flow ON/OFF" time periods. The light detector 55 signals are used in the processor circuit 60, thereby to log start and stop of fluid flow.

Figure 5:
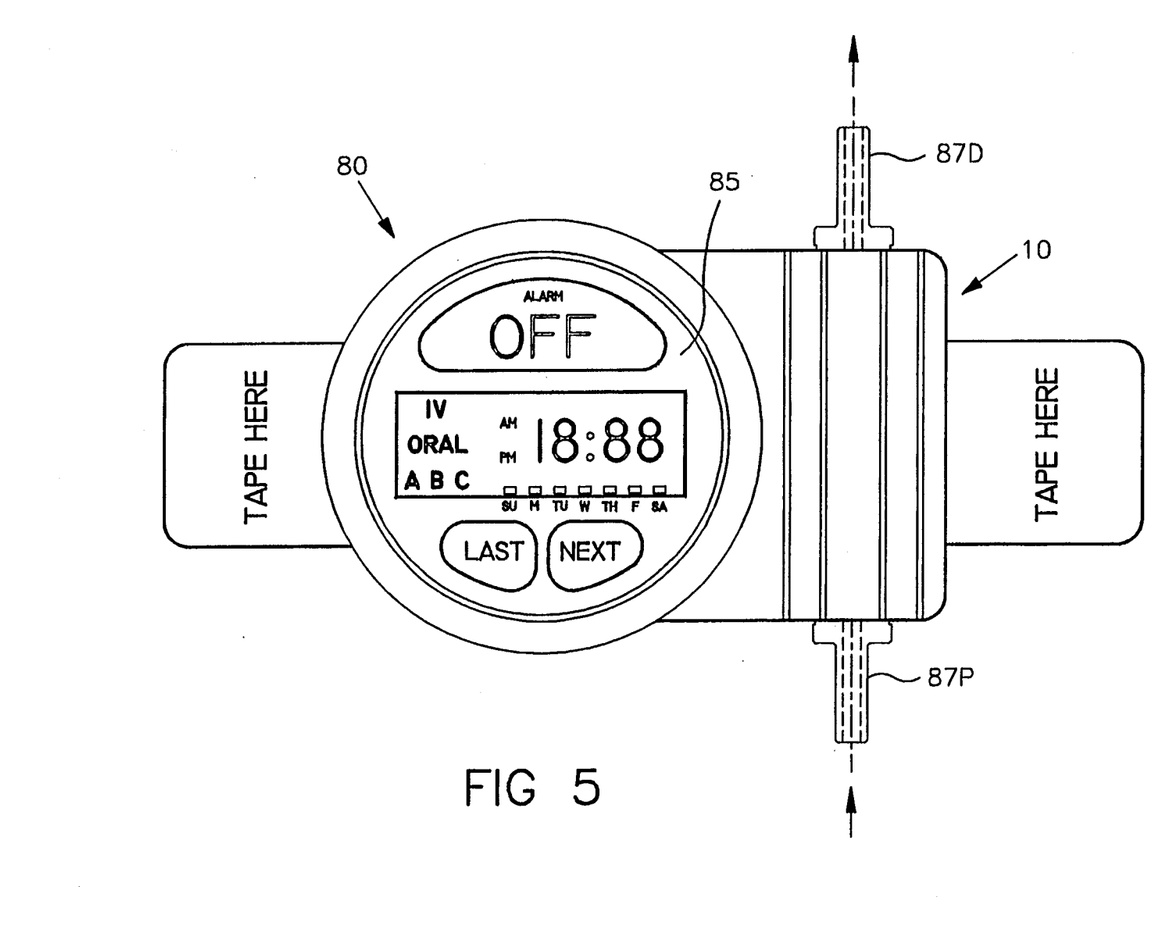
FIG. 5 is a view of the preferred layout of the face of a wrist watch sized event monitor housing of the invention.

The processor circuit 60 displays information concerning the infusion and other medication schedule and also the results of past IV activity on a liquid crystal display or other display apparatus. A clock 90 and an electronic storage means 95 are made a part of circuit 60 as necessary elements for identifying and recording the time of day at start, time of day at stop, and time of day at change in IV flow rate with each associated flow rate change. Results of IV activity may be caused to readout on display 85 or may be uploaded to a traditional computer system such as a PC or notebook computer with a serial communications port.

While the invention has been described with reference to a preferred embodiment, it is to be clearly understood by those skilled in the art that the invention is not limited thereto. Rather, the scope of the invention is to be interpreted only in conjunction with the appended claims.

What is claimed is:

1. An intravenous system for conducting an intravenous fluid, the system comprising:
   a flow indicator switch, including a fluid conductor having a transparent conical wall enclosing a fluid space extending between spaced apart proximal and distal annular shoulders, defining, respectively, inlet and outlet fluid orifices engaging the conductor, and, within the fluid space, an opaque movable stem body with a stem body biasing means providing a restoring force urging the stem body against the proximal shoulder, and further, a light emitter and a light sensor positioned in opposition lateral to the stem body and external to the fluid conductor, and further still, an opaque mask positioned between the light emitter and the light sensor, defining a narrow path for light to move from the light emitter, across the inlet fluid orifice to the light sensor; such that with no fluid flow, the stem body abutting the proximal shoulder, light transfer to the sensor is fully blocked by the stem body, while with a fluid flow, the stem body is moved away from the proximal shoulder, light transfer to the sensor is enabled, the sensor providing a sensor electrical signal identifying start and stop of fluid flow in the conductor.

2. The intravenous system of claim 1 further including a processor circuit providing an electrical sensor interconnected with the light sensor for sensing the sensor electrical signal, a clock for identifying the time of day of each start and stop of the fluid flow, an electronic storage means for storing time of day at start and time of day at stop and further including a visible display providing means for reading fluid flow state, type of medication scheduled, and time of next medication.

3. The intravenous system of claim 1 wherein the stem body is an elongated generally circular element having a generally flat surface at one end configured for general contact with the proximal annular shoulder, said contact not preventing intravenous fluid flow out of the fluid conductor through the inlet orifice, the stem body being displaceable from the proximal annular shoulder by fluid flow into the fluid conductor through the inlet orifice against the biasing means restoring force.

4. The intravenous system of claim 2 further including a wristwatch size case containing and integrating the flow indicator switch, the processor circuit and the display, said display positioned for ease of viewing from the exterior of the case, and further including inlet and outlet interconnection means for attachment of fluid conductors from a source of intravenous fluid and to an intravenous discharge device respectively.

5. The intravenous system of claim 1 wherein the mask includes a linearly sequenced plurality of further narrow paths providing light from the source to a corresponding linearly sequenced plurality of further light detectors positioned in opposition to the light source and lateral to the stem body and external to the fluid conductor, such that the longitudinal position of the stem body is known.

6. The intravenous system of claim 3 wherein the stem body includes a generally circular outer surface, the surface providing a series of fluidic pathways for conducting the fluid between the stem body and the conical wall providing improved conductance of the fluid in the fluid conductor.

7. The intravenous system of claim 6 wherein the outer surface of the stem body is cylindrical and the outer wall is conical in shape.

8. The intravenous system of claim 1 wherein the movable stem body is optically clear.

9. The intravenous system of claim 1 wherein the physical clearance between the movable stem body and the proximal shoulder allows fluids to be either moved into or withdrawn from the system.

10. The intravenous system of claim 1 wherein the static line pressure of the fluid is the same both upstream and downstream of the movable stem body irrespective of the position of the movable stem body.

* * * * *